United States Patent [19]

Charney et al.

[11] 4,389,313
[45] Jun. 21, 1983

[54] CHROMATOGRAPHIC COLUMN WITH IMPROVED SEALS

[75] Inventors: Andrew R. Charney, State College; Paul W. Kercher, Pennsylvania Furnace; Stanley A. Stone, State College, all of Pa.

[73] Assignee: Scientific Systems, Inc., State College, Pa.

[21] Appl. No.: 328,907

[22] Filed: Dec. 9, 1981

[51] Int. Cl.³ ............................................. B01A 15/02
[52] U.S. Cl. .................................... 210/198.2; 55/386
[58] Field of Search ................ 210/198.2, 232; 55/386

[56] References Cited

U.S. PATENT DOCUMENTS

| | | | |
|---|---|---|---|
| 4,026,803 | 5/1977 | Abrahams et al. | 210/198.2 |
| 4,083,702 | 4/1978 | Hartigan et al. | 55/67 |
| 4,162,977 | 7/1979 | Guillemin et al. | 210/198.2 |
| 4,187,177 | 2/1980 | Stahl | 210/198.2 |
| 4,257,894 | 3/1981 | Barney | 210/232 |
| 4,283,280 | 8/1981 | Brownlee | 210/198.2 |
| 4,289,620 | 9/1981 | Hara | 210/198.2 |

Primary Examiner—John Adee
Attorney, Agent, or Firm—C. Hercus Just

[57] ABSTRACT

This invention pertains to a chromatographic column and seal structure applicable to at least one end of a packed tubular column and formed either from metal or very hard plastic material such as a polyamidearamide resin, the seal members per se which are formed from such materials having a body circular in cross-section with a straight-through passage from end-to-end of uniform diameter and an annular rib on the body intermediately of opposite end portions, one of which is cylindrical for press-fitting into one end of the tubular column and the other end being frusto-conical and tapering away from the rib. A fitting or coupling is connectable to the end of the column by being threaded thereto and is provided with a seat against which one end of the rib of the seal abuts and also a dead space cavity inward from the seat which is conically complementary to the frusto-conical end of the seal and receives the same in close conformity when the fitting or coupling is tightly threaded against the end of the column and thereby tightly clamps the rib of the seal between the seat in the fitting and the end of the column.

7 Claims, 9 Drawing Figures

CHROMATOGRAPHIC COLUMN WITH IMPROVED SEALS

BACKGROUND OF THE INVENTION

The present invention pertains to a chromatographic column and the manner in which one or more ends of the column is connected to fittings or other columns and the like by means of highly efficient seal members capable of sustaining relatively high pressures, details of the structure being set forth below.

Chromatography is a process now used extensively and increasingly in analytical and preparative chemistry and wherein a stationary porous material is held in a chamber, such as a long column, while a mobile fluid material, either liquid or gaseous, is passed through the porous material. As an example, the stationary material can be an inert powder coated with a stationary liquid agent for which various distinct chemical compounds have varying affinities and, as the fluid moves through said column, the various compounds are delayed varying times by their contact with said stationary liquid agent, whereby the various chemicals emerge from the column at different times and can be detected individually by a refractometer, or other type of similar analytical apparatus relative to which the liquid flows when leaving the chromatographic column.

In chromatographic column connections to fittings and the like, which have been employed heretofore, problems have been associated with the design and use of suitable fields which are capable of remaining in fully sealed condition against pressures ranging, for example, between 1,000 and 10,000 psi, which are the ranges of pressures frequently used in liquid chromatography. Some of the sealed mechanisms developed heretofore are of such nature that when they are tightened into suitable sealing relationship, either the passage through the seal members or the end of the column which is clamped to a fitting or the like is deformed in undesirable manner, thereby necessitating the replacement of such seals, columns, or otherwise, from time to time.

In an effort to achieve appropriate seals, previous activities in the development of chromatographic equipment have resorted to various structures, some of which are relatively complex, as can be seen from the following patents which are illustrative of types of chromatographic column fittings and sealing means, at least some of which are presently in use:

U.S. Pat. No. 4,026,803—Abrahams et al—May 31, 1977
U.S. Pat. No. 4,083,702—Hartigan et al—Apr. 11, 1978
U.S. Pat. No. 4,162,977—Guillemin et al—July 31, 1979
U.S. Pat. No. 4,283,280—Brownlee—Aug. 11, 1981

The foregoing patents show various types of seals used heretofore, especially between the ends of chromatographic columns and fittings and the like connected to one or both ends thereof. The present invention is directed primarily to details and designs of sealing mechanisms which are of a relatively simple nature but highly effective to withstand the range of pressures presently employed in chromatographic apparatus. Advantages and details of the same are set forth below, as follows:

SUMMARY OF THE INVENTION

It is the principal object of the present invention to provide a seal member for chromatographic columns and apparatus which particularly is seated and clamped between at least one end of a chromatographic column and a seat in a fitting or other similar member which is threadably connected to one end of the column in a manner to tightly and effectively clamp the seal member between said seat and end of the column by means of an annular rib having opposite surfaces respectively engaged by said seat and end of the column without substantially deforming or in any other way changing the shape and size of the straight-through opening extending through the seal member between the opposite ends thereof.

It is another object of the invention to form said annular rib on the body of the seal member intermediately between the opposite end portions of the seal member which is circular in cross-section and one end portion of the seal member is substantially cylindrical throughout its length for preferably being press-fitted into one end of a chromatographic column and the other end portion of the seal member is frusto-conical and tapers away from said annular rib for close distribution thereof within a complementary cavity formed in a fitting to be attached to said chromatographic column.

A further object of the invention is to provide said aforementioned annular rib on the seal member with opposite faces which are parallel to each other.

Still another object of the invention is to provide one planar face on said aforementioned annular rib and the opposite face of said rib is in the form of a relatively flat frustum of a cone and joins one end of the cylindrical end portion of said seal member.

A still further object of the invention is to provide said frusto-conical end portion of the seal member with a short cylindrical extension on the outer end thereof.

Still another object of the invention is to provide the aforementioned cylindrical end portion of the seal member with a cavity of predetermined length extending into said portion from the outer end thereof and adapted to receive retaining means for the packing material in the chromatographic column to retain the same in said column.

Details of the foregoing objects and of the invention, as well as other objects thereof, are set forth in the following specification and illustrated in the accompanying drawings comprising a part thereof.

DETAILED DESCRIPTION OF THE PREFERRED EMBODIMENTS

Figure 1:
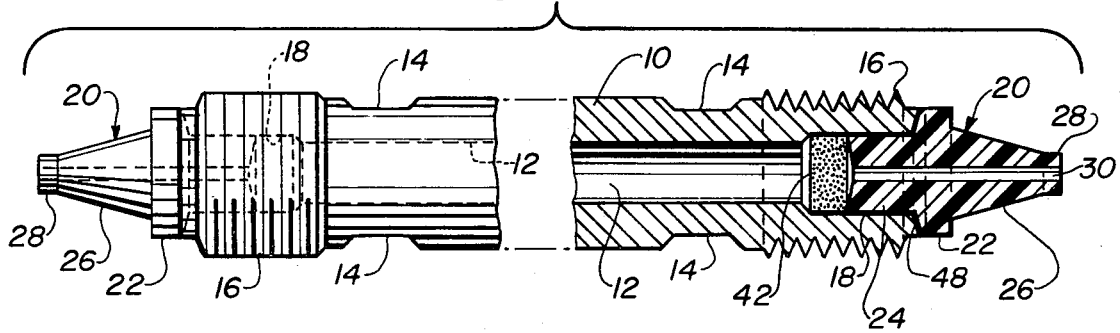
FIG. 1 is a foreshortened side elevation, partly in section, of an exemplary chromatographic column in the opposite ends of which seal members embodying the present invention are mounted in operative manner.

Referring to FIG. 1, there is illustrated therein an exemplary chromatographic column 10 which is tubular and includes a longitudinal opening of uniform diameter within which conventional packing, such as used in chromatographic operations, is contained in conventional density. For convenience of operation, one or both of the opposite end portions of the column 10 may be provided with opposing flat surfaces 14 for engagement of a wrench therewith incident to tightening the column into a fitting and under which circumstances the fitting normally is engageable by a wrench to facilitate the connection of the fitting to one end of such column. The outer end portions 16 are externally threaded and the outermost end portions of the longitudinal opening 12 are reamed or otherwise are machined to provide a smooth cylindrical surface 18 for purposes described below.

Figure 2:
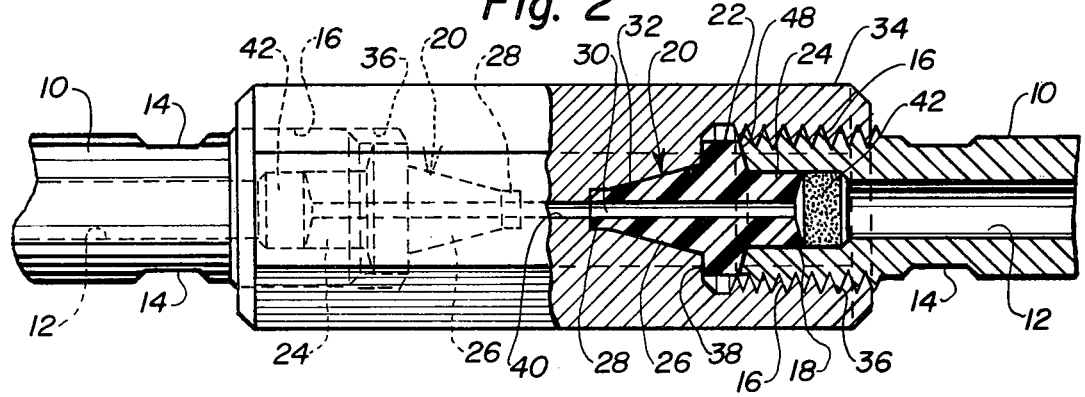
FIG. 2 is a fragmentary side elevation, showing fragmentary end portions of chromatographic columns respectively connected to sockets in the opposite ends of a fitting comprising a coupling member, one fragmentary end portion of said arrangement being shown in vertical section to illustrate details.
Figure 3:
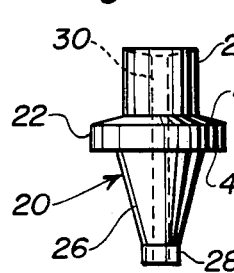
FIGS. 3–6 respectively are side elevations of different embodiments of seal members incorporating the principles of the invention.
Figure 4:
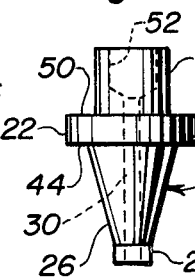
Figure 5:
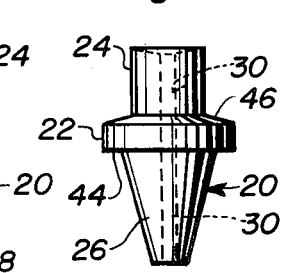
Figure 6:
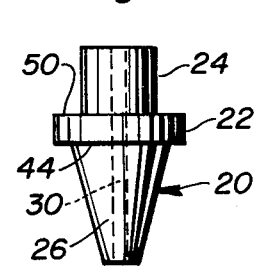

One of the most important elements of the present invention comprises the seal member 20, one embodiment of which is illustrated in FIGS. 1–3 and other embodiments of which are respectively illustrated in FIGS. 4, 5, and 6. The seal members are circular in cross-section and intermediately of the opposite end portions thereof, there is an integral annular rib 22. One end portion 24 of the seal member is cylindrical in shape for purposes of preferably being press-fitted into the smooth cylindrical surface 18 in the end of the column 10 and the opposite end portion 26 is frusto-conical and tapers away from the annular rib 22. Also, in the embodiment shown in FIGS. 1–3, the frusto-conical end portion 26 terminates in a short cylindrical extremity 28. The seal member 20 is provided with a central straight-through passage 30 extending between the opposite ends thereof and of uniform diameter.

The seal member 20 is formed very precisely from one of several useful kinds of material, one of these being stainless of which the preferred type is identified in the trade as 316SS. Another suitable type of material is a polyamidearamide resin, one type of which is sold under the trade name Vespel SP-21, which is sold by the DuPont Company, and is so identified in their sales catalogue.

The purpose of the precise formation of the seal member 20 is particularly that the cylindrical end portion 24 thereof may be press-fitted into the cylindrical surface 18 in the end of the column 10 and the frusto-conical end portion 26 thereof closely conforms to a cavity 32 in fitting 34, which is complementary in shape to the frusto-conical end portion 26. The cavity 32 is sometimes referred to in the trade as "dead space", and the positioning of the frusto-conical end portion 26 of the seal member 20 therein very closely fills said space.

The fitting 34, which is illustrated in FIG. 2, is provided in opposite ends thereof with internally threaded bores 36 into which the threaded outer end portions 16 of the column 10 are threaded for purposes of the outermost end of the column 10 engaging one face of the annular rib 20, while the opposite face of said rib flatly abuts a seat 38 which adjoins the frusto-conical cavity 32. By such clamping arrangement which occurs against the opposite faces of the annular rib 22, a highly effective and efficient seal is formed between the column 10 and the fitting 34 in order that the material to be subjected to the column 10 and the packing therein may move at precise rate through the central passage 30 of the seal member 20, and as will be seen in FIG. 2, the fitting 34 which, essentially in exemplary manner, comprises a coupling to connect two chromatographic columns 10, is provided with a central passage 40, whereby the material being treated readily can be passed between the interconnected chromatographic columns 10, as illustrated in FIG. 2.

Especially for purposes of retaining the packing material within the longitudinal opening 12 of the column 10, the embodiment of the invention illustrated in FIGS. 1 and 2 includes material retaining means 42, which also is seated in the surface portion 18 formed in the outer end of column 10. Said retaining means may be in the form of a suitable frit or any other appropriate material capable of permitting passage of the material being treated but retaining the packing material within the interior of the column 10.

As stated hereinabove, the seal member 20 may be made from relatively hard metal, such as Type 316 stainless steel, or selectively, may also be made from an exemplary specified polyamidearamide resin, such as forementioned Vespel. This particular resin, although quite hard, might be considered relatively soft compared to the metal specified above, but nevertheless, the hardness of said resin is sufficient that it is highly capable of maintaining the uniform diameter of the central passage 30 in the seal member 20, when securely clamped operatively between the fitting 34 and the column 10. Such clamped connection is capable of withstanding pressures up to 10,000 psi without leakage, whether the seal member is formed either from metal or resin of the types referred to above.

Referring to FIGS. 3–6, it will be seen that FIG. 3 illustrates in side view a seal member 20 of the same shape as that illustrated in FIGS. 1 and 2. In this embodiment of seal member, it will be seen that the face 44 of the annular rib 22 is planar, while the opposite face 46 is slightly frusto-conical for purposes of firmly abutting the chamfered end 48 of the column 10 as shown, for example, in FIGS. 1 and 2, such formation being preferred at least in certain types of chromatographic columns.

In FIG. 4, the embodiment of the seal member 20 shown therein is modified from that shown in FIG. 3, in that the surface 50 of the annular rib 22 which is adjacent the cylindrical end portion 24 also is planar and parallel to the opposite planar face 44. This embodiment is especially adapted to have the planar surface 50 firmly abut an end surface of the column 10, which is planar and perpendicular to the axis of the column. Further, the embodiment in FIG. 4 also is provided in the cylindrical end portion 24 with an inwardly extending recess 52 within which material retaining means may be positioned to serve similarly as the retaining means 42, shown in FIGS. 1 and 2.

The embodiment shown in FIG. 5 is similar to that shown in FIG. 3, except that the short cylindrical extremity 28 of FIG. 3 has been removed from the embodiment in FIG. 5. In FIG. 6, said embodiment is similar to that shown in FIG. 4, except that it does not contain the cavity 52 and, as in FIG. 5, the short cylindrical extremity 28 has been omitted.

Figure 7:
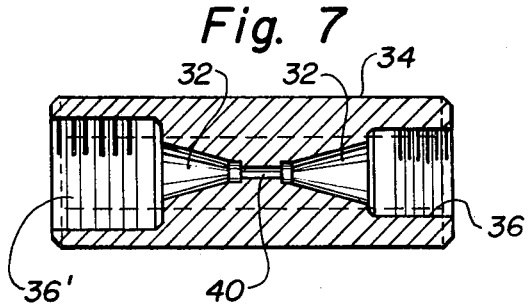
FIG. 7 is a vertically sectioned illustration of a fitting similar to the one illustrated in FIG. 2, but in which the sockets respectively in opposite ends thereof are of a different diameter to accommodate correspondingly different sizes of chromatographic columns.
Figure 8:
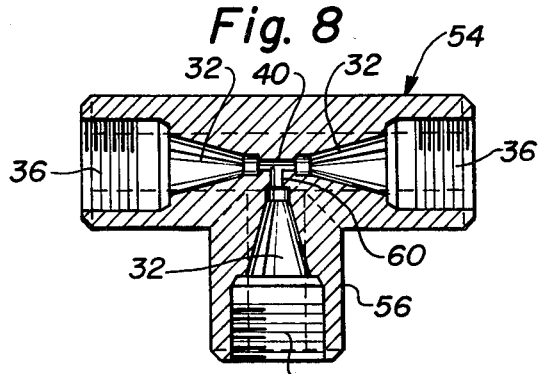
FIG. 8 is a vertically sectioned view of a tee and in the stems of which threaded cavities are formed in conjunction with intercommunicating conical cavity portions for accommodation of a plurality of chromatographic columns, the ends of which respectively are threaded into the threaded cavities shown in the tee.

In FIGS. 7 and 8, two exemplary representative types of fittings and couplings are illustrated which embody the principles of the present invention. In FIG. 7, the specifically illustrated embodiment includes in opposite ends thereof, internally threaded bores 36 and 36', which respectively are of different diameters for purposes of connecting chromatographic columns of different diameters. Otherwise, the fitting 34 shown in said figure is similar to that shown in FIG. 2.

In FIG. 8, a further example of fitting is shown in the form of a tee 54, and in which the upper part thereof is similar to the fitting 34 shown in FIG. 2, but a central, laterally extending branch 56 is formed thereon, having an internally threaded bore 58 formed therein and communicating with a frusto-conical cavity 32, and also having a branch internal passage 60, which intersection communicates with the passage 40 between the frusto-conical cavities 32 in the upper portion of the tee.

Figure 9:
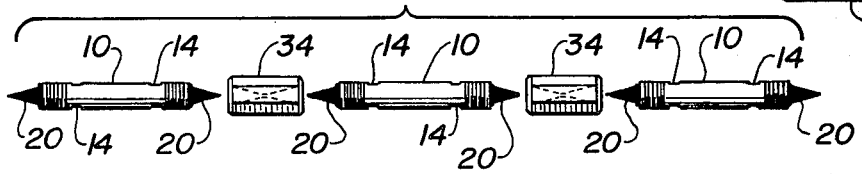
FIG. 9 is an exploded, diagrammatic illustration of a series of exemplary chromatographic columns adapted to be interconnected by fittings, such as shown in FIGS. 2 and 7, or otherwise.

Referring to FIG. 9, there is illustrated therein somewhat diagrammatically, a series of chromatographic columns 10, which are adapted to be connected to each other in end-to-end relationship by means of exemplary fittings 34, the opposite ends of the columns 10 having seal members 20 affixed thereto, which may be of any one of the various embodiments shown in the preceding figures, especially FIGS. 3-6, as desired, depending upon the type preferred for a specific use. For purposes of facilitating the connection of the fittings 34 to the ends of the columns 10, it is preferred that the exterior transverse shape of the fittings be of a suitable geometric figure to provide faces engageable by a wrench, or at least have a pair of parallel flats formed respectively on opposite sides for such purpose.

From the foregoing, it will be seen that the present invention provides for use with chromatographic columns very simple but highly effective and efficient seal member designs represented in a limited number of embodiments thereof, but all including the basic features described hereinabove and illustrated in the drawings. Ease of assembly is afforded incident to obtaining tight clamping of the annular ribs 22 between circular opposing clamping surfaces, such as the seat 38 in the fittings and the outer end of the column 10, which may either be flat or chamfered, as desired.

The foregoing description also illustrates a column system for chromatography in which the seal members 20 cooperate with opposite ends of the column 10, especially when packed with desired particulate material, to form closures for the ends of the column to prevent exposure of the packing to ambient atmosphere and also retain the packing within the column incident to the column system being connected to appropriate adaptor fittings and connectors, whereby the column system can be adapted for connection to products of various manufacturers of different types of chromatography equipment and systems.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

What is claimed is:

1. A chromatographic column comprising in combination:
   (1) a tubular column cartridge having at least one end threaded exteriorly and the interior of said end being arranged to receive one end of a seal member,
   (2) a column seal member attachable to said at least one end of said column cartridge and comprising:
      a. a body circular in cross-section and having a central straight-through passage from end-to-end of uniform diameter and also having opposite end portions,
      b. an annular rib on said body intermediately of the end portions thereof and provided with opposed surfaces to be clamped,
      c. one end portion of said body being substantially cylindrical and complementary to and receivable within said one end of said column cartridge,
      d. the other end portion of said body being frusto-conical and tapering away from said rib,
   (3) an apertured coupling having a cavity in one end complementary to the exterior of said other end portion of said body and adapted to receive the same in sealing relationship,
   (4) a seat in said cavity, and
   (5) threads in the cavity of said coupling complementary to the exterior threads on said one end of said column and operable to threadably receive the same and connect at least one end of said column cartridge to the cavity end of said coupling in a manner to clamp the annular rib of said seal member to said column cartridge and said coupling by the clamping surfaces of said annular rib being clampingly engaged between said threaded end of said column cartridge and said seat in the cavity of said coupling and said frusto-conical end of said seal member closely filling said cavity inwardly from said seat therein.

2. The chromatographic column according to claim 1 in which the opposite surfaces of said annular rib of said seal member to be clamped are substantially planar and parallel to each other.

3. The chromatographic column according to claim 1 in which one of said surfaces of said annular rib on said seal member to be clamped is in the form of a relatively flat taper extending toward and connected to the cylindrical end portion of said seal member.

4. The chromatographic column according to claim 1 further including a short cylindrical extension on the outer end of the frusto-conical end portion of said seal member.

5. The chromatographic column according to claim 1 in which the end of said tubular column which receives the cylindrical end of said seal member is provided with a cylindrical cavity extending inwardly a predetermined distance to receive said cylindrical end of said seal member and communicating with the central passage in said circular body, and said cylindrical cavity extending a short distance beyond the inner end of said cylindrical end of said seal member to accommodate porous means to retain packing material in said tubular column.

6. The chromatographic column according to claim 1 in which said cylindrical end portion of said body of said seal member is press-fitted into said one end of said tubular column.

7. The chromatographic column according to claim 1 in which said seal member is formed by molding plastic material having a hardness adequate to resist deformation of said straight-through passage in said seal when said seal member is securely clamped as aforesaid in tightly sealed condition.

* * * * *